United States Patent [19]

Lee et al.

[11] 4,344,190

[45] Aug. 17, 1982

[54] PLUGS FOR THE MEDULLARY CANAL OF A BONE

[75] Inventors: Alan J. C. Lee; Robin S. M. Ling, both of Exeter, England

[73] Assignee: University of Exeter, Devon, England

[21] Appl. No.: 171,309

[22] Filed: Jul. 23, 1980

[30] Foreign Application Priority Data

Jul. 25, 1979 [GB] United Kingdom ................ 7925892

[51] Int. Cl.³ ............................. A61F 1/00; A61F 1/24
[52] U.S. Cl. ............................................. 3/1.9; 3/1.91;
3/1.913; 128/92 C; 128/92 CA
[58] Field of Search ................. 3/1.9, 1.91, 1.912,
3/1.913; 128/92 C, 92 CA, 92 G

[56] References Cited

U.S. PATENT DOCUMENTS

| | | | |
|---|---|---|---|
| 3,924,274 | 12/1975 | Heimke et al. | 3/1.91 |
| 4,245,359 | 1/1981 | Stuhmer | 3/1.91 X |
| 4,274,163 | 6/1981 | Malcom et al. | 3/1.91 |

FOREIGN PATENT DOCUMENTS

| | | |
|---|---|---|
| 6480 | 1/1980 | European Pat. Off. |
| 7819583 | 11/1978 | Fed. Rep. of Germany |
| 1325128 | 3/1963 | France |
| 1409053 | 10/1975 | United Kingdom |
| 2017503 | 10/1979 | United Kingdom |

OTHER PUBLICATIONS

Advertising Brochure "Have You Got Time on Your Hands?", Howmedica International, Inc.
"Properties of Bovine Fibrin Absorbable Implants", Capperauld, Ian et al., 01/77, vol. 144.3-7
"Biethium-Sterile Absorbable Ox Fibrin Prosthesis".
"Compression Moulded Ox Fibrin as a Potentially Valuable Biomaterial", by Ian Capperauld MB FRCSEd.

Primary Examiner—Ronald L. Frinks
Attorney, Agent, or Firm—Larson and Taylor

[57] ABSTRACT

An implant 22, e.g. for locating a hip prosthesis, is placed in the medullary canal 18 of a bone 20 (e.g. the femur) and secured by pressurized cement 24. A push-fit plug 10 prevents cement penetrating down the canal. The plug can be biodegradable so that in time it dissolves away and does not modify the flexural rigidity of the cement/bone system and the risk of fractures occurring at the level of the plug is reduced. Additionally or alternatively, the outwardly facing end portion 16 of the plug may be generally conical so that the thickness of the cement increases gradually and the flexural rigidity likewise changes gradually.

14 Claims, 2 Drawing Figures

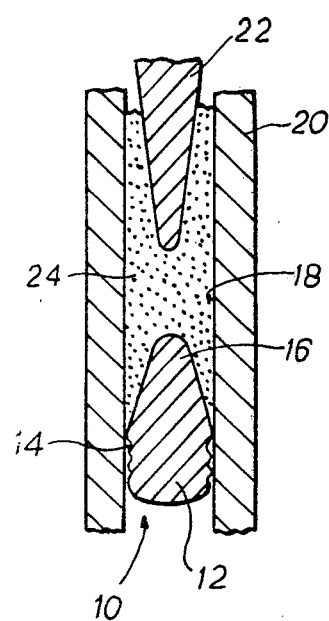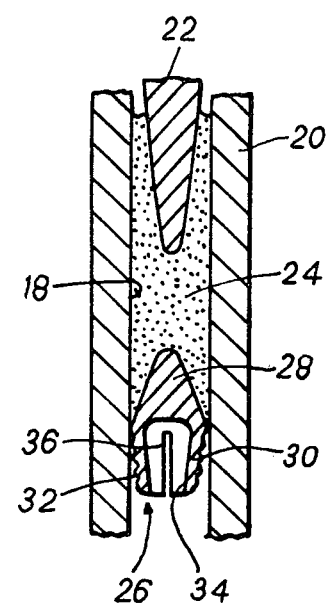

PLUGS FOR THE MEDULLARY CANAL OF A BONE

BACKGROUND TO THE INVENTION

This invention relates to surgery in which an implant is placed in the medullary canal of a bone, and more particularly to plugs for insertion in the medullary canal in such surgery.

An implant has to be placed in the medullary canal of a femur when a patient is to be given an artificial hip joint, in order to locate the hip prosthesis. The implant is located in the medullary canal by use of a bone cement, e.g. polymethylmethacrylate cement. Such cement does not have any appreciable adhesive qualities, and relies for its security on obtaining a mechanical interlock with irregularities in the bone. Such mechanical interlocking is greatly enhanced if the cement is introduced into the canal under pressure. However, there is a tendency for the cement to flow down the medullary canal so it is not possible to use much pressure. To overcome this, it is known to insert a plug which is a push fit inside the medullary canal and which prevents the cement flowing down the canal and permits greater pressurisation of the cement. It is known for such plugs to be formed from bone, or from bone cement. An improved plug made from a plastics material is the Seidel plug. Such a plastics plug will of course remain inside the medullary canal when the surgery is completed. A problem with all such known plugs is that because of such factors as the difference in Young's modulus between the bone and the bone cement, there is an abrupt change in the flexural rigidity of the bone at the plug. This has not uncommonly led to fractures at the level of the plug, for example if the patient should suffer a fall. A fracture at this level is very difficult to set.

SUMMARY OF THE INVENTION

According to one aspect of the present invention we provide a plug for the medullary canal of a bone, having a portion with sides adapted to be a push fit in the medullary canal, the plug being made of a biodegradable material.

Preferably the plug has a tapering end portion, which preferably is generally conical. The plug can then be inserted in the medullary canal with the conically tapering portion facing into the part of the canal into which cement is to be introduced, so that when the cement is introduced the conically tapering portion forms a mould so that there is a gradually increasing thickness of cement in contact with the bone along the length of the tapering portion. This can then provide a gradual change in flexural rigidity of the cement/bone system along the plug. Being biodegradable, the plug will eventually dissolve, and so have no effect on flexural rigidity.

According to a second aspect of the invention we provide a plug for the medullary canal of a bone, comprising a portion having sides adapted to be a push fit in the medullary canal, and a tapering end portion, preferably a generally conically tapering end portion. This plug can be of plastics material. The portion which has sides adapted to be a push fit in the medullary canal may be hollow, and may also have one or more slits in a longitudinal plane which permit flexing of said sides to facilitate insertion in the canal.

BRIEF DESCRIPTION OF THE DRAWINGS AND DESCRIPTION OF PREFERRED EMBODIMENTS

In the accompanying drawings,

FIGS. 1 and 2 are schematic sectional views of two plugs embodying the invention, in situ in a bone.

Referring to FIG. 1, the plug 10 has a generally cylindrical portion 12 with generally parallel serrated sides 14. The sides 14 merge into a generally conically tapered portion 16 of the plug. During surgery, the medullary canal 18 of the bone 20 such as a femur will be reamed out, and a plug 10 of suitable size for the reamed out canal will be introduced with the cylindrical portion 12 leading so that the conically tapering portion 16 faces outwardly. The portion 12 is a push fit inside the canal 18, assisted by the serrations 14, and the plug is inserted for a sufficient distance to permit filling of the canal with cement as desired.

Bone cement 24, e.g. polymethylmethacrylate bone cement, is introduced into the open end of the medullary canal 18, suitably by retrograde filling above the plug 10, and pressurised. The desired implant 22 such as a hip prosthesis is then introduced into the medullary canal 18 by being inserted down the centre of the previously placed bone cement. Further pressurisation of the bone cement is achieved at this stage by occluding the top of the medullary canal and allowing the generally wedge-shaped stem of the implant to force bone cement further into the medullary canal of the femur. Pressurisation of the cement ensures that it is forced into the intertrabecular space of the bone structure thereby providing a good mechanical interlock so as to anchor the implant securely. The plug 10 prevents pressurised cement flowing further down the medullary canal.

Because the conically tapering portion 16 of the plug faces into the reamed out cavity of the canal 18 which is filled with cement, it forms a mould for the cement so that the thickness of cement which is in contact with and mechanically interlocking with the bone 20 increases gradually along the length of the tapering portion 16. This means that the flexural rigidity of the cement/bone system also changes gradually in this region. The risk of the bone fracturing in this region is therefore reduced.

The plug 10 is manufactured from a biodegradable material comprising stabilised ox fibrin, mixed with 35% glycerol as a plasticizer. This material is described by Ian Cappernauld, P. Lawrie and D. A. French in "Properties of Bovine Fibrin Absorbable Implants", Surgery: Gynecology & Obstetrics, January 1977, Vol. 144, 3–7. It is available from Ethnor Division, Ethicon Limited, P.O. Box 408, Bankhead Avenue, Edinburgh, EH11 4HE, under the Trade Mark BIETHIUM. The plug 10 can be made by compression moulding the powdered material, or by machining from a round bar. Other biodegradable materials could of course be used. Because it is made of biodegradable material, the plug 10 eventually dissolves, leaving behind the cement 24 with its gradually increasing thickness around the region once occupied by the portion 16. Once this has happened, the flexural rigidity of the cement/bone system is unmodified by the plug, and so the risk of a fracture occuring in this area is reduced even further.

Referring now to FIG. 2, a plug 26 is shown which is moulded in the usual way from a non-biodegradable plastics material. A suitable material is ultra-high molecular weight polyethylene. It is generally similar to the plug 10 shown in FIG. 1, and in particular has a conically tapering portion 28 which behaves in exactly the same manner as in FIG. 1. There is also a generally cylindrical portion 30 which has serrated sides 32 which are a push fit in the medullary canal 18, as before. However, the portion 30 is hollowed out to give a recess 34 open at the end of the plug remote from the portion 28. Two slits 36 are provided through the walls of the portion 30, the slits being open at the end of the plug remote from the portion 28, and being in a longitudinal plane with respect to the plug. This effectively divides the portion 30 into two halves which can flex slightly towards each other. This facilitates insertion of the plug 26 into the canal 18.

What is claimed is:

1. A plug for the medullary canal of a bone, said plug being adapted to be a push fit in a medullary canal and comprising a first elongate portion having elongate sides and a second elongate portion extending from one end of said first portion and tapering gradually inwardly along its length in the direction away from said first portion, said plug being adapted to be push fit into a medullary canal of a bone with said first portion leading such that said second portion extends into the portion of the canal into which bone cement can be introduced for locating an implant in the medullary canal whereby, when bone cement is introduced into the canal, the gradually tapering portion of said plug forms a mould so that there is a gradually increasing thickness in cement in contact with the bore along the length of the tapering portion in the direction away from said first elongate portion.

2. A plug according to claim 1 made from plastics material.

3. A plug according to claim 1 made from a biodegradable material.

4. A plug according to claim 3 wherein the biodegradable material comprises ox fibrin.

5. A plug according to claim 4 wherein the biodegradable material contains glycerol as a plasticizer.

6. A plug according to claim 1 wherein the first portion is hollow.

7. A plug according to claim 6 wherein the hollow first portion has one or more slits in a longitudinal plane which permit flexing of said sides to facilitate insertion in the canal.

8. A plug according to claim 1 wherein the tapering second portion is generally conical.

9. In a plug for the medullary canal of a bone constructed and arranged to be push fit in a medullary canal of a bone such that, when in place, the plug is able to overcome the tendency of bone cement, under pressure in the medullary canal, to flow down the canal, the improvement wherein said plug is made of a biodegradable material.

10. A plug according to claim 9 wherein the biodegradable material comprises ox fibrin.

11. A plug according to claim 10 wherein the biodegradable material contains glycerol as a plasticizer.

12. In a method of placing an implant in a medullary canal of a bone, comprising the steps of inserting a plug in the medullary canal and introducing cement into the canal outwardly of the plug for securing the implant, so that the plug helps to prevent the penetration of cement down the canal, the improvement wherein said plug comprises a first elongate portion having elongate sides adapted to be a push fit in a medullary canal and a second elongate portion extending from one end of said first portion and tapering gradually inwardly along its length in the direction away from said first portion and is inserted in the canal with the tapering end portion facing outwardly so as to act as a mould for the cement.

13. A method according to claim 12 wherein the plug is made of a biodegradable material.

14. In a method of placing an implant in a medullary canal of a bone, comprising the steps of inserting a plug in the medullary canal, said plug being constructed and arranged to be push fit in said medullary canal such that, when in place, the plug is able to overcome the tendency of bone cement, under pressure in the medullary canal, to flow down the canal, and introducing cement into the canal outwardly of the plug for securing the implant, the improvement wherein said plug is made of a biodegradable material.

* * * * *